United States Patent [19]

Bishop

[11] Patent Number: 5,613,500
[45] Date of Patent: Mar. 25, 1997

[54] RETRACTABLE PHLEBOTOMY NEEDLE

[76] Inventor: Steve Bishop, P.O. Box 1289, Ft. Worth, Tex. 76101-1289

[21] Appl. No.: 391,579

[22] Filed: Feb. 21, 1995

[51] Int. Cl.$^6$ ........................................................ A61B 5/00
[52] U.S. Cl. ............................ 128/763; 128/760; 604/110
[58] Field of Search .................................. 128/760, 763; 604/110, 187, 239, 240, 164

[56] References Cited

U.S. PATENT DOCUMENTS

| | | | |
|---|---|---|---|
| 4,813,426 | 3/1989 | Haber et al. | 128/763 |
| 4,984,580 | 1/1991 | Wanamaker | 128/763 |
| 5,046,508 | 9/1991 | Weissler | 128/763 |
| 5,049,133 | 9/1991 | Pascuel | 604/240 X |
| 5,125,414 | 6/1992 | Dysarz | 128/763 |
| 5,167,641 | 12/1992 | Schmitz | 604/196 |
| 5,180,370 | 1/1993 | Gillespie | 604/110 |
| 5,190,526 | 3/1993 | Murray et al. | 604/110 |
| 5,221,628 | 5/1993 | Marshall | 604/110 |
| 5,403,286 | 4/1995 | Lokwood, Jr. | 128/763 X |
| 5,423,586 | 6/1995 | Shaw | 128/763 X |
| 5,447,501 | 9/1995 | Karlsson et al. | 128/763 X |

*Primary Examiner*—Sam Rimell
*Attorney, Agent, or Firm*—Norman B. Rainer

[57] ABSTRACT

A multi-sample blood collection needle device is provided with safety features that minimize the possibility of an accidental needle-stick. The device includes a rigid shroud that secures a stationary rear hollow needle, and a forward needle telescopically mounted upon the rear needle. A coil spring causes the forward needle to retract rearwardly upon the stationary rear needle, thereby disposing the point of the forward needle safely within the shroud.

8 Claims, 2 Drawing Sheets

RETRACTABLE PHLEBOTOMY NEEDLE

BACKGROUND OF THE INVENTION

1. Field of the Invention

This invention concerns a device for use by a health care technician for collecting blood specimens from patients, and more particularly relates to a multi-sample blood collection needle device which minimizes the possibility of needle-stick accidents after use.

2. Description of the Prior Art

Devices for withdrawing blood specimens from patients and causing said blood to directly enter a sealed storage vial have been in use for many years. Such devices have, for example, been marketed under the trademark Vacutainer by the Becton-Dickinson Company of New Jersey, and under the trademark Venoject by the Kimbell-Ternmo Company of California. These blood-collecting devices are generally comprised of a hollow needle sharpened at a forward, patient application extremity and at a rearward extremity, and a connector hub mounted upon the needle. The connector hub is adapted to threadably engage the front extremity of a circular cylindrical adapter having an open back extremity. The needle is thereby positioned upon the center axis of the adapter, disposing the rearward extremity of the needle about one third of the distance proceeding into the cylinder toward said open back extremity.

In use, an elongated circular cylindrical collection tube is employed, having a closed bottom extremity and opposed mouth extremity sealed with a rubber stopper. The collection tube contains a vacuum and has an outside diameter which permits close-fitting insertion into said adapter. When the forward extremity of the needle has entered the patent's vein, the collection tube is pressed forwardly, causing the rearward extremity of the needle to pierce the rubber stopper. The evacuated condition of the tube causes blood to flow into the tube. The tube containing the blood specimen is then removed, whereupon the resilient characteristics of the rubber stopper automatically re-seal the mouth extremity of the collection tube. By virtue of such construction and use, the barrel member merely serves to align the needle with the collection tube, and does not come into contact with the blood. Accordingly, the same barrel member may be employed repeatedly.

Contamination by accidental needle sticks has generated a plethora of inventions in the syringe field, particularly with the increased risk of exposure of medical personnel to AIDS contaminated needles. Some of the "safety" syringes designed to reduce risk of accidental sticks are seen in U.S. Pat. Nos. 5,167,641; 5,180,370; 5,190,526 and 5,211,628. In general, such devices employ coil springs which retract the needle into the tubular housing of the syringe.

It is to be noted that, although syringes are somewhat related in design to Vacutainer-type blood collecting devices, there are significant differences, especially in the design of the needle and manner of function of the devices. Syringes are designed primarily for injecting substances into a patient. If used to remove a blood specimen, as was the practice long ago, the specimen would have to be transferred to a separate collection container, and the barrel and plunger of the syringe would then either be discarded or sterilized prior to re-use.

The current manner of use of Vacutainer-type devices is such that, once the blood specimen has been collected, the needle is withdrawn from the patient's vein and is placed point first in a sharps container. The needle is then unscrewed from the adapter and deposited into the container, and the adapter is set aside for re-use. The problem with such manner of use is that, after withdrawing the needle from the patient, there is a period of time during which the needle point is exposed. It is during this time period that inadvertent needle sticks occur.

The recent prior art includes a safety-modified Vacutainer wherein a plastic sleeve/shroud is slipped down over the needle after it is withdrawn, and is then locked into place onto the adapter. However, there is still the risk interval from the instant of removal of the needle from the patient to its securement by the shroud. In addition, the entire apparatus, including the adapter, is discarded, which represents increased costs.

It is accordingly an object of the present invention to provide a Vacutainer-type blood-collecting device which poses less risk to health-care personnel employing the device.

It is another object of this invention to provide a device as in the foregoing object which provides for substantially automatic retraction of the needle to a secured disposition.

It is a further object of the invention to provide a device of the aforesaid nature which permits re-use of the adapter component.

It is a still further object of this invention to provide a device of the aforesaid nature which is easy to use and of simple construction amenable to low cost manufacture.

These and other beneficial objects and advantages will be apparent from the following description.

SUMMARY OF THE INVENTION

The above and other beneficial objects and advantages are accomplished in accordance with the present invention by a needle assembly comprising:

a) a rigid shroud comprised of a circular cylindrical sidewall elongated upon a center axis between forward and rearward extremities, b) a centered aperture associated with said forward extremity, c) a connector hub associated with said rearward extremity, d) a stationary hollow needle secured by said connector hub upon said axis and extending between a forward extremity located within said shroud and a pointed rearward extremity located rearwardly of said connector hub, e) a forward hollow needle slideably positioned upon said stationary needle, slideably secured by said aperture, and extending between a pointed forward extremity initially disposed in front of said shroud, and a rearward extremity provided with an outwardly directed annular collar, f) a compressed coil spring disposed upon said forward needle within said shroud, and interactive between the forward extremity of said shroud and said collar, g) latching means interactive between said sidewall and collar resisting the urging of said spring, and h) means associated with said sidewall for releasing said latch means, whereby i) release of said latch means causes said spring to force said forward needle rearwardly upon said stationary needle until the pointed forward extremity of said forward needle is disposed within said shroud.

In preferred embodiments, the portion of said stationary needle extending rearwardly of said connector hub is encased in a pierceable sheath fabricated of rubber or equivalent material. The entire needle assembly is sterilized and preferably encased within a rigid protective enclosure that preserves sterility.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
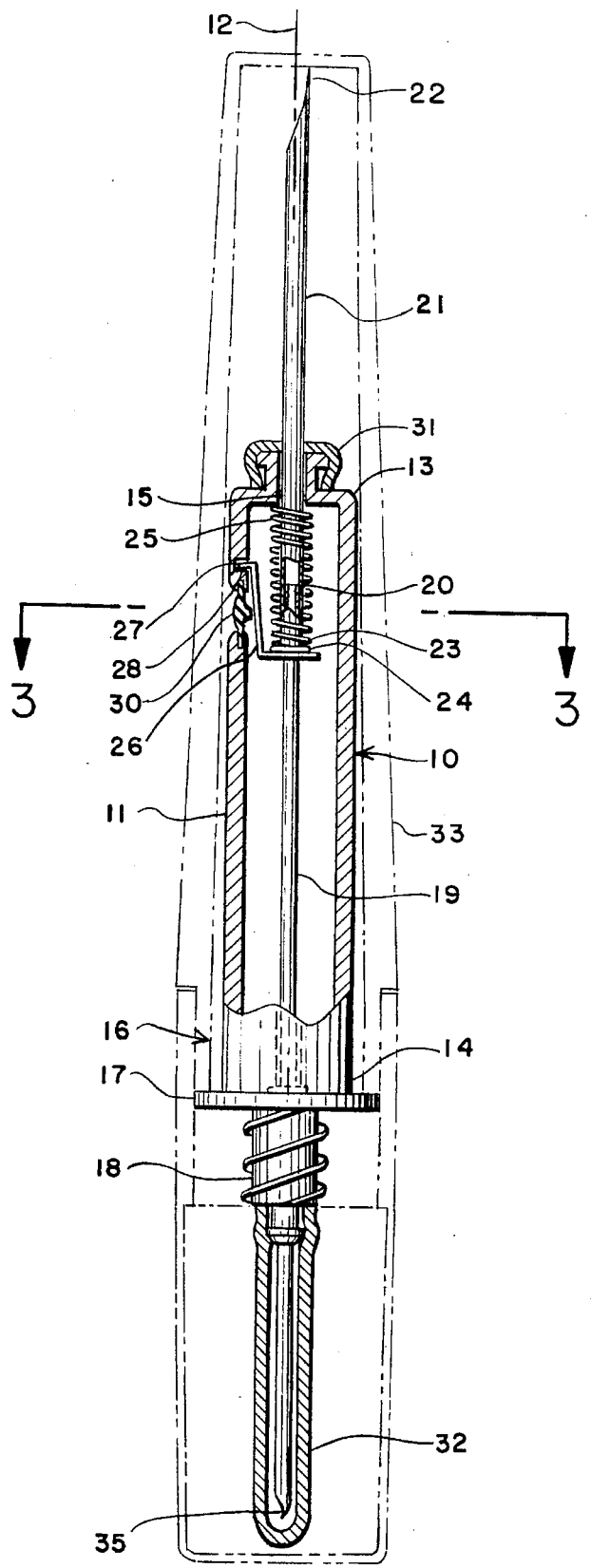
FIG. 1 is a longitudinal view, partly in section, of an embodiment of the needle assembly of the present invention shown in its unused state.
Figure 2:
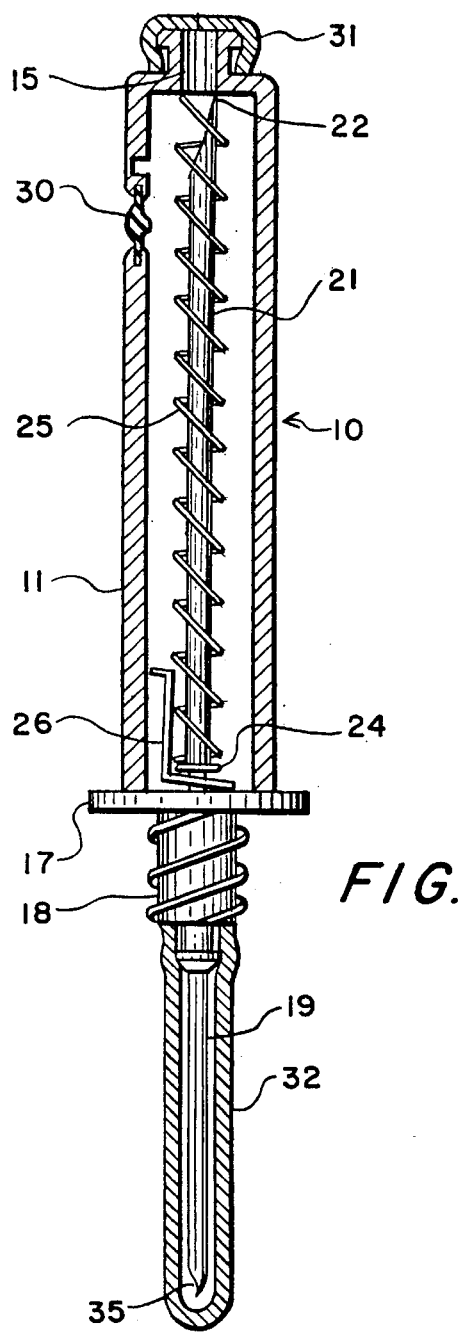
FIG. 2 is a similar view of the needle assembly of FIG. 1 shown in its used state.
Figure 3:
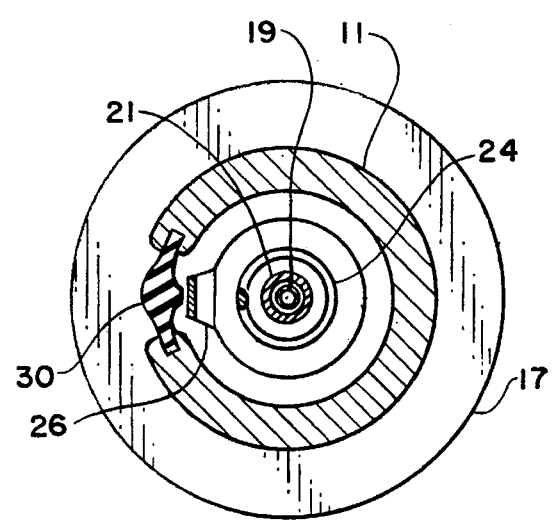
FIG. 3 is an enlarged sectional view taken in the direction of the arrows upon the line 3—3 of FIG. 1.

Referring to FIGS. 1–3, an embodiment of the needle assembly of the present invention is shown having a rigid shroud 10 comprised of circular cylindrical sidewall 11 elongated upon center axis 12 between forward and rearward extremities 13 and 14, respectively. An aperture channel 15, centered upon axis 12, is disposed within forward extremity 13. A connector hub 16 is associated with rearward extremity 14, said hub comprised of flange plate 17 that substantially seals the rearward extremity of said shroud, and threaded sleeve 18 rearwardly emergent from said plate as a continuous integral extension thereof.

A stationary hollow needle 19 is secured by hub 16 upon axis 12, and extends between a front extremity 20 located within said shroud, and a pointed back extremity 35 located rearwardly of hub 16. A pierceable rubber sheath 32 protectively encloses that portion of needle 19 extending rearwardly of hub 16.

A forward hollow needle 21 is positioned upon needle 19 in a telescopically slideable manner, and is further slideably secured by channel 15. Needle 21 extends between a pointed leading extremity 22 initially disposed in front of said shroud, and a trailing extremity 23 provided with outwardly directed annular collar 24.

A compressed coil spring 25 is disposed upon forward needle 21 within said shroud in abutting relationship between the forward extremity of said shroud and collar 24. Latch means in the form of bracket 26 is disposed within shroud 10, said bracket having a forward bent portion 27 that engages a notch 28 within sidewall 11. A bent rear shelf portion 29 of bracket 26 is disposed rearwardly of collar 24, and thereby prevents spring 25 from driving needle 21 rearwardly.

Means for releasing said bracket, in the form of resilient diaphragm 30, is disposed is said sidewall at a location radially adjacent bracket 26. Diaphragm 30 is joined to said sidewall in a manner achieving an impervious seal, and is sufficiently flexible so that finger pressure placed upon the exterior of the diaphragm can displace the diaphragm inwardly sufficiently to dislodge bent portion 27 of the bracket from notch 28. Such action causes spring 25 to force said forward needle rearwardly upon said stationary needle until the pointed extremity 22 is disposed within the shroud, as shown in FIG. 2.

An elastic cover 31 is disposed over channel 15 to provide an impervious seal with forward needle 21 in the starting state of the needle assembly shown in FIG. 1. The entire needle assembly is sterilized and removably encased within a rigid protective housing 33 that preserves sterility.

In use, the needle assembly is removed from housing 33, and is operatively connected by hub 16 with a conventional cylindrical Vacutainer adapter. A conventional collection tube is placed in readiness within the adapter. The leading extremity 22 of needle 21 is caused to pierce a patient's vein. The collection tube is then forced forwardly, causing penetration of sheath 32 by the pointed back extremity 35 of needle 19. Such action causes a blood specimen to enter the collection tube. Diaphragm 30 is then pressed, causing needle 21 to retract to a position of safety, as shown in FIG. 2. The shroud is then inserted downwardly into a sharps container and twisted, causing the needle assembly to fall directly into the sharps container.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A needle assembly comprising:

a) a rigid shroud comprised of a sidewall elongated upon a center axis between forward and rearward extremities, b) a centered aperture associated with said forward extremity, c) a connector hub associated with said rearward extremity, d) a stationary hollow needle secured by said connector hub upon said axis and extending between a front extremity located within said shroud and a pointed back extremity located rearwardly of said connector hub, e) a forward hollow needle slideably positioned upon said stationary needle, slideably secured by said aperture, and extending between a pointed leading extremity initially disposed in front of said shroud, and a trailing extremity provided with an outwardly directed annular collar, f) a compressed coil spring disposed upon said forward needle within said shroud, and interactive between the forward extremity of said shroud and said collar, g) latch means interactive between said sidewall and collar resisting the urging of said spring, and h) means associated with said sidewall for releasing said latch means, whereby i) release of said latch means causes said spring to force said forward needle rearwardly upon said stationary needle until the pointed leading extremity of said forward needle is disposed within said shroud.

2. The needle assembly of claim 1 further provided with a pierceable sheath that envelopes said stationary needle rearwardly of said connector hub.

3. The combination of the needle assembly of claim 2 and a rigid protective housing that encloses said needle assembly.

4. The combination of claim 3 in a sterilized condition.

5. The needle assembly of claim 2 wherein said connector hub is comprised of a flange that seals said rearward extremity and a threaded sleeve rearwardly emergent from said flange as a continuous integral extension thereof.

6. The needle assembly of claim 2 wherein said latch means is comprised of a bracket having a forward bent portion and a bent rear shelf portion interactive with said collar rearwardly thereof.

7. The needle assembly of claim 6 wherein said sidewall is provided with a notch adapted to secure the forward portion of said bracket.

8. The needle assembly of claim 1 wherein said centered aperture is a channel, and is provide with an elastic cover that provides an impervious seal with said forward needle.

* * * * *